(12) United States Patent
Hirokawa et al.

(10) Patent No.: US 7,985,291 B2
(45) Date of Patent: Jul. 26, 2011

(54) PERIMIDINE-SUBSTITUTED SQUARYLIUM DYE, DISPERSION MEDIUM, DETECTION MEDIUM AND IMAGE FORMING MATERIAL

(75) Inventors: Kazuhiko Hirokawa, Kanagawa (JP); Kazunori Anazawa, Kanagawa (JP); Yuka Ito, Kanagawa (JP); Minquan Tian, Kanagawa (JP); Suguru Nakaso, Kanagawa (JP); Shinji Hasegawa, Kanagawa (JP); Takashi Matsubara, Kanagawa (JP); Makoto Furuki, Kanagawa (JP); Miho Watanabe, Kanagawa (JP); Tomoko Miyahara, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 155 days.

(21) Appl. No.: 12/428,174

(22) Filed: Apr. 22, 2009

(65) Prior Publication Data

US 2010/0108949 A1   May 6, 2010

(30) Foreign Application Priority Data

Oct. 30, 2008   (JP) .................. 2008-279977

(51) Int. Cl.
*D21H 17/07* (2006.01)
(52) U.S. Cl. ........... 106/287.25; 106/287.2; 106/287.21; 106/287.23; 106/287.24; 546/66; 549/415; 562/505
(58) Field of Classification Search ............... 106/287.2, 106/287.21, 287.23, 287.24, 287.25; 546/66; 549/415; 562/505
See application file for complete search history.

(56) References Cited

U.S. PATENT DOCUMENTS

| | | | | |
|---|---|---|---|---|
| 5,360,694 A | * | 11/1994 | Thien et al. | 430/200 |
| 5,380,635 A | * | 1/1995 | Gomez et al. | 430/517 |
| 5,763,134 A | * | 6/1998 | Busman et al. | 430/157 |
| 6,124,075 A | * | 9/2000 | Ishihara et al. | 430/270.18 |
| 6,444,415 B1 | * | 9/2002 | Tanaka et al. | 430/517 |
| 6,482,950 B1 | * | 11/2002 | Garcia et al. | 546/66 |
| 7,235,351 B2 | * | 6/2007 | Fukusaka et al. | 430/353 |

FOREIGN PATENT DOCUMENTS

| | | |
|---|---|---|
| JP | 10-36695 A | 2/1998 |
| JP | 2004-264448 A | 9/2004 |
| JP | 2005-82507 A | 3/2005 |

* cited by examiner

*Primary Examiner* — Jill Warden
*Assistant Examiner* — Monique Cole
(74) *Attorney, Agent, or Firm* — Sughrue Mion, PLLC (57) ABSTRACT

A perimidine-substituted squarylium dye is represented by the following formula (I):

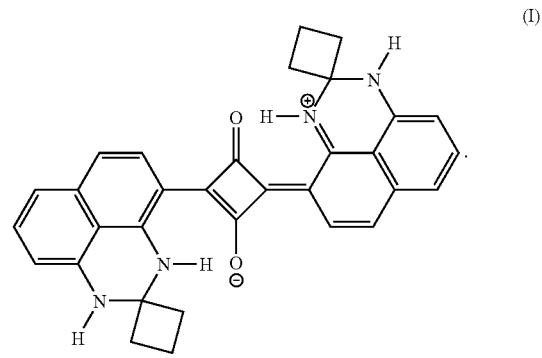

(I)

6 Claims, 3 Drawing Sheets

PERIMIDINE-SUBSTITUTED SQUARYLIUM DYE, DISPERSION MEDIUM, DETECTION MEDIUM AND IMAGE FORMING MATERIAL

CROSS-REFERENCE TO RELATED APPLICATIONS

This application is based on and claims priority under 35 USC 119 from Japanese Patent Application No. 2008-279977 filed on Oct. 30, 2008.

BACKGROUND

1. Technical Field

The present invention relates to a perimidine-substituted squarylium dye, a dispersion medium, a detection medium and an image forming material.

2. Related Art

Organic near-infrared absorbing materials have an advantage in absorption coefficient over inorganic near-infrared absorbing materials, and surpass inorganic ones in number of molecular species. Examples of a color material known as an organic near-infrared absorbing material include naphthalocyanine dyes, croconium dyes and cyanine dyes.

SUMMARY

According to an aspect of the invention, there is provided a perimidine-substituted squarylium dye represented by the following formula (I):

BRIEF DESCRIPTION OF THE DRAWINGS

Exemplary embodiment(s) of the present invention will be described in detail based on the following figures, wherein.

DETAILED DESCRIPTION

Preferred embodiments of the invention are illustrated below. Herein, drawings are referred to depending on the circumstances. Incidentally, the same numeral or sign is given to the same or corresponding parts in the drawings, and repeated descriptions are omitted.

(Perimidine-Substituted Squarylium Dye)

The perimidine-substituted squarylium dye of the invention is represented by the following formula (I):

It can be safely said that the perimidine-substituted squarylium dye represented by the formula (I) is almost invisible to the human eye because of its sufficiently low absorbance in the visible-radiation wavelength region of 400 to 750 nm, and besides, the dye of the formula (I) can change its infrared absorption characteristic in the region of 850 nm when receives external stimulation, such as irradiation with ultraviolet rays, and this change can be detected even with inexpensive CCDs in contrast to changes in other wavelength ranges. Herein, the expression of "almost invisible to the human eye" should not be construed as referring only to the state of being not at all perceivable through the human eye, but it is intended that, like materials which are known as the so-called invisible color materials and capable of forming dot patterns on printing paper or so on, materials close to transparent or those having very poor absorption in the visible region fit into the category of materials "almost invisible to the human eye". Moreover, the perimidine-substituted squarylium dye represented by the formula (I) retains its invisibility both before and after it achieves a change in infrared absorption characteristic, so even after use in security application it has no fear of being noticed and visually identified. In other words, the present dye has a great ability to conceal itself.

The perimidine-substituted squarylium dye represented by the formula (I) originally shows its infrared absorption maximum ($\lambda_{max}$) at 811 nm as measured in the form of a molecular dispersion liquid (dispersion medium: tetrahydrofuran (THF)), but when irradiated with, say, an ultraviolet (UV) lamp (Mineralight Lamp UVGL-25, trade name, a product of UVP Inc., wavelength: 365 nm, radiation illuminance: 2 mV/cm$^2$) in a specified amount of energy (about 0.84 J/cm$^2$, the energy corresponding to 7-minute irradiation), it changes its $\lambda_{max}$ to 850 nm. This wavelength change is irreversible, and after the dye once has changed its $\lambda_{max}$, it never returns to its original state. This irreversible wavelength change is supposed to be caused by cleavage of the four-membered rings in the formula (I) under irradiation with ultraviolet rays. By utilization of this property, the present perimidine-substituted squarylium dye can be used e.g. as a medium for detection of ultraviolet rays.

The perimidine-substituted squarylium dye represented by the formula (I) can be prepared according to e.g. a reaction scheme as shown below.

More specifically, the perimidine intermediate (a) can be prepared by allowing 1,8-diaminonaphthalene and cyclobutanone to react with each other in the presence of a catalyst under conditions of azeotropic reflux in a solvent (Process (A-1)). Examples of a catalyst usable in Process (A-1) include p-toluenesulfonic acid monohydrate, benzenesulfonic acid monohydrate, 4-chlorobenzenesulfonic acid hydrate, pyridine-3-sulfonic acid, ethanesulfonic acid, sulfuric acid, nitric acid and acetic acid. Examples of a solvent usable in Process (A-1) include alcohol compounds and aromatic hydrocarbons. The perimidine intermediate (a) can be purified by high-performance column chromatography or recrystallization.

Next, the perimidine intermediate (a) is allowed to react with 3,4-dihydroxycyclobuta-3-ene-1,2-dione (referred to as "squaric acid" or "quadratic acid" too) under conditions of azeotropic reflux in a solvent, thereby preparing the perimidine-substituted squarylium dye represented by the formula (I) (Process (A-2)). It is preferred that Process (A-2) be performed in an atmosphere of nitrogen gas.

Examples of a solvent usable in Process (A-2) include alcohol compounds such as 1-propanol, 1-butanol and 1-pentanol, aromatic hydrocarbons such as benzene, toluene, xylene and monochlorobenzene, ethers such as tetrahydrofuran and dioxane, halogenated hydrocarbons such as chloroform, dichloroethane, trichloroethane and dichloropropane, and amides such as N,N-dimethylformamide and N,N-dimethylacetamide. Although alcohol compounds may be used alone, other solvents like aromatic hydrocarbons, ethers, halogenated hydrocarbons or amides are preferably used in conditions that they are mixed with alcohol compounds. Examples of a preferred solvent include 1-propanol, 2-propanol, 1-butanol, 2-butanol, a solvent mixture of 1-propanol and benzene, a solvent mixture of 1-propanol and toluene, a solvent mixture of 1-propanol and N,N-dimethylformamide, a solvent mixture of 2-propanol and benzene, a solvent mixture of 2-propanol and toluene, a solvent mixture of 2-propanol and N,N-dimethylformamide, a solvent mixture of 1-butanol and benzene, a solvent mixture of 1-butanol and toluene, a solvent mixture of 1-butanol and N,N-dimethylformamide, a solvent mixture of 2-butanol and benzene, a solvent mixture of 2-butanol and toluene, and a solvent mixture of 2-butanol and N,N-dimethylformamide. When such a solvent mixture is used, it is preferable that the concentration of an alcohol solvent is at least 1% by volume, especially from 5% to 75% by volume.

The mole ratio of the perimidine intermediate (a) to 3,4-dihydroxycyclobuta-3-ene-1,2-dione (the number of moles of the perimidine intermediate (a)/the number of moles of 3,4-dihydroxycyclobuta-3-ene-1,2-dione) in Process (A-2) is preferably from 1 to 4, far preferably from 1.5 to 3. While the mole ratios smaller than 1 tend to lower the yield of the perimidine-substituted squarylium dye represented by the formula (I), the mole ratios greater than 4 worsen the availability of the perimidine intermediate (a) and tend to make it difficult to isolate and purify the perimidine-substituted squarylium dye represented by the formula (I).

In addition, the use of a dehydrating agent in Process (A-2) tends to reduce the reaction time and enhance the yield of the perimidine-substituted squarylium dye represented by the formula (I). The dehydrating agent used herein has no particular restriction t so long as it reacts with neither the perimidine intermediate (a) nor 3,4-dihydroxycyclobuta-3-ene-1,2-dione, and suitable example thereof include orthoformates such as trimethyl orthoformate, triethyl orthoformate, tripropyl orthoformate and tributyl orthoformate, molecular sieve and the like.

Although it varies depending on the kind of the solvent used, the reaction temperature in Process (A-2) is preferably 60° C. or higher, particularly preferably 75° C. or higher. When the solvent used is e.g. a solvent mixture of 1-butanol and toluene, the temperature of the reaction solution is preferably from 75° C. to 105° C.

In addition, the reaction time in Process (A-2) varies depending on the kind of the solvent used or the temperature of the reaction solution. When the reaction is carried out e.g. under conditions that the solvent used is a solvent mixture of 1-butanol and toluene and the temperature of the reaction solution ranges from 90° C. to 105° C., the reaction time is preferably from 2 to 4 hours.

The perimidine-substituted squarylium dye produced in Process (A-2), which is represented by the formula (I), can be purified by cleaning with a solvent, high-performance column chromatography or re-crystallization.

(Dispersion Medium and Detection Medium)

The dispersion medium according to the invention contains the present perimidine-substituted squarylium dye represented by the formula (I). The present dispersion medium may be either a dispersion medium prepared by dissolving or dispersing the perimidine-substituted squarylium dye into a solvent or a dispersion medium prepared by dispersing the perimidine-substituted squarylium dye into a polymer.

The solvent usable in the dispersion medium, though not limited to particular one so long as the perimidine-substituted squarylium dye can be dissolved or dispersed therein, is e.g. tetrahydrofuran (THF), acetone or the like.

The polymer usable in the dispersion medium has no particular restriction so long as the perimidine-substituted squarylium dye can be dispersed therein, and examples thereof include polyester, styrene-acrylic resin and acrylic resin.

The detection medium according to the invention includes the present dispersion medium in a state of being held to a holding member that is ultraviolet ray transmissive, and detects that the dispersion medium has undergone the exposure to ultraviolet rays.

Figure 1:
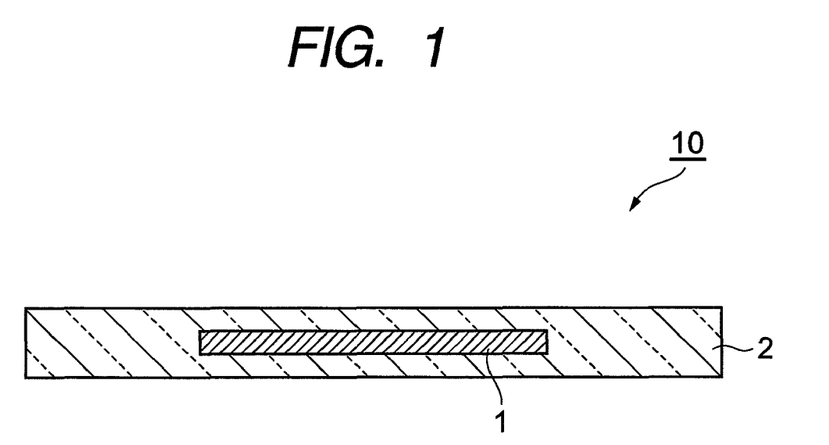
FIG. 1 is a schematic cross-sectional view depicting an exemplary embodiment of the detection medium according to the invention.

FIG. 1 is a schematic cross-sectional diagram showing an exemplary embodiment of the present detection medium. The detection medium 10 shown in FIG. 1 includes (seals up) the dispersion medium 1 containing the perimidine-substituted squarylium dye represented by the formula (I) in the holding member 2 that is ultraviolet ray transmissive. The perimidine-substituted squarylium dye represented by the formula (I) changes its infrared absorption characteristic when exposed to ultraviolet rays, and the once-caused change is irreversible. Therefore, the detection medium 10 can be used as a detection medium endowed with traceability which can indicate e.g. that a sealed article has been opened, and it has undergone exposure to external light including ultraviolet rays or the like.

At this time, the use of a material absorbing ultraviolet rays in a specified amount as the holding member 2 allows the specified amount of ultraviolet absorption to be utilized as the threshold value of the detection. On the other hand, when a detection target has a designated packaging or the like, the ultraviolet absorption by the detection target proper can be in itself detected by equating the ultraviolet absorbance of the holding member 2 and that of the packaging material. When a detection target is a substance susceptible to ultraviolet rays, such as a medicine, the substance is generally packed in a vial or with a kind of wrapping or packing material. So, in order to determine what extent of ultraviolet rays in real terms the substance has been exposed to, subtraction of the amount of ultraviolet rays absorbed by the packing material or the like must be considered. This subtraction of the amount of ultraviolet rays absorbed by the packing material or the like can be performed automatically without calculation, provided that a detection target is wrapped with a holding member 2 having the same amount of ultraviolet absorption as the packing material has.

To mention one aspect of the detection medium 10 shown in FIG. 1, a thin-film glass or vitreous silica cell in which a 0.01 to 0.1 mass % THF solution of the present perimidine-substituted squarylium dye is sealed up is prepared as the dispersion medium 1, and this dispersion medium 1 is enclosed in a seal as the holding member 2, thereby forming the detection medium 10. And this detection medium 10 is adopted as a UV-exposure detection seal and stuck on a substance targeted for detection of whether or not the substance will have undergone UV-exposure.

In another aspect of the detection medium 10, a substance prepared by dispersing the present perimidine-substituted squarylium dye into a polymer, such as polyester or styrene-acrylic resin, in a concentration of 0.01% to 0.1% by mass is prepared as the dispersion medium 1, and enclosed in a seal as the holding medium 2, thereby forming the detection medium 10. And this detection medium 10 is adopted as a UV-exposure detection seal and stuck on a substance targeted for detection of whether or not the substance will have undergone UV-exposure.

Such a detection medium 10 is stuck on an object of UV-exposure detection, submitted to a UV-exposure test, and then measured for its infrared absorption characteristic by means of a spectrometer capable of measuring absorption in the infrared region. When the detection medium 10 has undergone exposure to ultraviolet rays of specified energy or above, a shift in infrared absorption wavelength can be detected.

Alternatively, the presence or absence of such a shift can be detected simply by use of two CCDs having centers of their individual sensitivities at 800 nm and 850 nm, or such a shift can also be measured through detection of the presence or absence of the shift to 850 nm by using a CCD having the center of its sensitivity at 850 nm after filtering out wavelengths of 830 nm or shorter.

(Image Forming Material)

The image forming material according to the invention is a material containing the perimidine-substituted squarylium dye represented by the formula (I). Such an image forming material allows detection of UV exposure in common with the dispersion medium and the detection medium.

In the image forming material relating to an exemplary embodiment of the invention, it is preferable that the perimidine-substituted squarylium dye represented by the formula (I) is contained in the form of particles. Since the perimidine-substituted squarylium dye has great intermolecular interaction and particles thereof have high crystallinity, light fastness of the image forming material can be further enhanced by containing the dye in the form of particles.

Particles of the perimidine-substituted squarylium dye represented by the formula (I) can be formed e.g. as follows. The purified product after Process (A-2) is dissolved in tetrahydrofuran, the resulting solution forms a precipitate on injection into ice-cold distilled water with stirring by means of a syringe or the like, and the precipitate is filtered off by suction, washed with distilled water, and then subjected to vacuum drying. Thus, the intended particles can be obtained. In this manner, the particle size of the precipitate can be controlled to the desired range by adjusting the concentration of the perimidine-substituted squarylium dye represented by the formula (I) in the solution, the injection speed of the solution, the amount or temperature of the distilled water, the stirring speed, or/and so on. The median diameter d50 of particles of the perimidine-substituted squarylium dye represented by the formula (I) is preferably from 50 nm to 300 nm, far preferably from 80 nm to 150 nm. When the median diameter d50 is smaller than 50 nm, light fastness of the dye particles tends to become low; while, when the median diameter d50 is greater than 300 nm, the dye particles tends to cause a reduction in infrared absorption efficiency and an increase in influence of scattering.

In addition to the perimidine-substituted squarylium dye represented by the formula (I), the image forming material relating to an exemplary embodiment of the invention can contain other ingredients as mentioned below. However, from the viewpoint of ensuring sufficient responsivity and invisibility, the content of the perimidine-substituted squarylium dye represented by the formula (I) is preferably from 0.05% to 3% by mass, far preferably from 0.1% to 2% by mass, based on the total solids content in the image forming material.

The image forming material relating to an exemplary embodiment of the invention has no particular restrictions as to its uses, but preferable uses thereof are as electrophotographic toner, inkjet printer ink, ink for letterpress printing, offset printing, flexographic printing, gravure printing or silk-screen printing, and so on.

When it is electrophotographic toner, the image forming material relating to an exemplary embodiment of the invention may be used by itself as a one-component developer, or may be used as a two-component developer in combination with a carrier. The carrier usable herein includes heretofore known ones. For instance, a resin-coated carrier having a resin coating on a core material can be used. In this resin coating, electrically conductive powder or the like may be dispersed.

When it is electrophotographic toner, the image forming material relating to an exemplary embodiment of the invention can contain a binding resin. Examples of a binding resin usable herein include homopolymers or copolymers synthesized from styrene monomer such as styrene or chlorostyrene, monoolefin such as ethylene, propylene, butylene or isoprene, vinyl ester monomer such as vinyl acetate, vinyl propionate, vinyl benzoate or vinyl butyrate, α-methylene aliphatic monocarboxylic acid ester monomer such as methyl acrylate, ethyl acrylate, butyl acrylate, dodecyl acrylate, octyl acrylate, phenyl acrylate, methyl methacrylate, ethyl methacrylate, butyl methacrylate or dodecyl methacrylate, vinyl ether monomer such as vinyl methyl ether, vinyl ethyl ether or vinyl butyl ether, or/and vinyl ketone monomer such as vinyl methyl ketone, vinyl hexyl ketone or vinyl isopropenyl ketone. Of these binding resins, especially typical ones include polystyrene, styrene-alkyl acrylate copolymer, styrene-alkyl methacrylate copolymer, styrene-acrylonitrile copolymer, styrene-butadiene copolymer, styrene-maleic anhydride copolymer, polyethylene, polypropylene and the like. In addition, polyester, polyurethane, epoxy resin, silicone resin, polyamide, denatured rosin, paraffin wax and the like can also be used as binding resins.

When it is electrophotographic toner, the image forming material relating to an exemplary embodiment of the invention can further contain a charge controlling agent, an offset inhibitor and so on as required. The charge controlling agent includes those which are used in positive charging and those which are used in negative charging. In positive charging, quaternary ammonium salts can be used. On the other hand, examples of a charge controlling agent usable in negative charging include metal complexes of alkylsalicylic acid, charge controlling agents of polar group-containing resin type and the like. Examples of an offset inhibitor usable therein include low-molecular-weight polyethylene and low-molecular-weight polypropylene.

When the image forming material relating to an exemplary embodiment of the invention is electrophotographic toner, inorganic powdery particles or organic particles may be added as an external additive to the toner surface for the purposes of enhancing flowability and powder storage stability, controlling frictional electrification, improving transfer capability and cleaning capability, and so on. Examples of inorganic powdery particles include known ones such as silica, alumina, titania, calcium carbonate, magnesium carbonate, calcium phosphate and cerium oxide. Further, known types of surface treatment may be given to those powdery inorganic particles in accordance with the intended purpose. On the other hand, examples of organic particles include emulsion polymerization products containing as their individual constituents vinylidene fluoride, methyl methacrylate, a combination of styrene and methyl methacrylate, and so on, or soap-free polymers.

When it is inkjet printer ink, the image forming material relating to an exemplary embodiment of the invention can take the form of aqueous ink which contains water. In order to prevent drying of ink and improve ink permeability, the image forming material relating to an exemplary embodiment of the invention can further contain a water-soluble organic solvent. Examples of such an organic solvent include polyhydric alcohols such as ethylene glycol, diethylene glycol, polyethylene glycol and glycerin, N-alkylpyrrolidones, esters such as ethyl acetate and amyl acetate, lower alcohols such as methanol, ethanol, propanol and butanol, and glycol ethers such as ethylene oxide or propylene oxide adducts of methanol, butanol and phenol. Either one kind or more than one kind of organic solvent may be used. The organic solvent(s) to be used may be chosen as appropriate in consideration of hygroscopicity, moisture retention, solubility of the perimidine-substituted squarylium dye represented by the formula (I), permeability, viscosity of ink, freezing temperature and so on. The organic solvent content in the inkjet printer ink is preferably from 1% to 60% by mass.

When it is inkjet printer ink, the image forming material relating to an exemplary embodiment of the invention can contain additives hitherto known as ingredients of ink in order to satisfy miscellaneous requirements for inkjet printer systems. Examples of such additives include a pH adjusting agent, a resistivity adjusting agent, an antioxidant, an antiseptic, a fungicide and a metal blocking agent. Examples of a pH adjusting agent include alcoholamines, ammonium salts and metal hydroxides. Examples of a resistivity adjusting agent include organic salts and inorganic salts. Examples of a metal blocking agent include chelating agents.

When it is inkjet printer ink, the image forming material according to the invention can also contain a water-soluble resin, such as polyvinyl alcohol, polyvinyl pyrrolidone, carboxymethyl cellulose, styrene-acrylic acid resin or styrene-maleic acid resin, in such an amount as to cause neither clogging of jet nozzles nor change in discharge direction of ink.

When it is ink for letterpress printing, offset printing, flexographic printing, gravure printing or silk-screen printing, the image forming material relating to an exemplary embodiment of the invention can take the form of oil ink containing a polymer and an organic solvent. Examples of such a polymer include natural resins such as protein, rubber, cellulose, shellac, copal, starch and rosin, thermoplastic resins such as vinyl resin, acrylic resin, styrene resin, polyolefin resin and novolak phenol resin, and thermosetting resins such as resol-type phenol resin, urea resin, melamine resin, polyurethane resin, epoxy resin and unsaturated polyester. Examples of an organic solvent which can be contained therein include those recited in the description of inkjet printer ink.

When it is ink for letterpress printing, offset printing, flexographic printing, gravure printing or silk-screen printing, the image forming material according to the invention can further contain additives, such as a plasticizer for enhancement of the elasticity and strength of printed film, a solvent for adjustment of viscosity and enhancement of drying properties, a drying agent, a viscosity adjusting agent, a dispersing agent and various reacting agents.

EXAMPLES

The invention will now be illustrated more concretely by reference to Examples and Comparative Examples, but the following examples should not be construed as limiting the scope of the invention in any way.

Example 1

(Synthesis of Perimidine-Substituted Squarylium Dye)

A solution prepared by mixing 4.843 g (98%, 30.0 mmol) of 1,8-diaminonaphthalene, 2.523 g (98%, 36 mmol) of cyclobutanone and 24 mg (0.127 mmol) of p-toluenesulfonic acid monohydrate with 45 ml of toluene is heated up to 95° C. with stirring in an atmosphere of nitrogen gas and kept for 3 hours in this condition. Thereafter, the solution is refluxed at 140° C. for 5 hours. And the water produced in the reaction is removed by component distillation. After the conclusion of the reaction, a dark brown solid obtained by distilling the toluene out of the reaction solution is dissolved in and extracted with acetone, purified by re-crystallization from acetone, and further dried at 110° C. Thus, 5.2 g of a brown solid as the intermediate is obtained (in 83% yield).

A solution prepared by mixing 1.89 g (9 mmol) of the intermediate obtained and 913 mg (8.0 mmol) of 3,4-dihydroxycyclobuta-3-ene-1,2-dione with 16 mL of n-butanol and 48 mL of toluene is heated up to 70° C. with stirring in an atmosphere of nitrogen gas, and kept for 3 hours in this condition. Thereafter, the solution is refluxed at 140° C. for 3 hours, thereby running reaction. The water produced in the reaction is removed by component distillation. After the conclusion of the reaction, most of the solvents are distilled away in an atmosphere of nitrogen gas, and the reaction mixture obtained is added to 30 mL of hexane with stirring. The thus formed blackish brown precipitate is filtered off by suction, washed with hexane and dried, thereby yielding a blackish blue solid. This solid is washed with successive ethanol, acetone, a 60% aqueous solution of ethanol, ethanol and acetone. Thus, 3.5 g (80% yield) of perimidine-substituted squarylium dye represented by the formula (I) is obtained in the form of a blackish blue solid.

Figure 2:
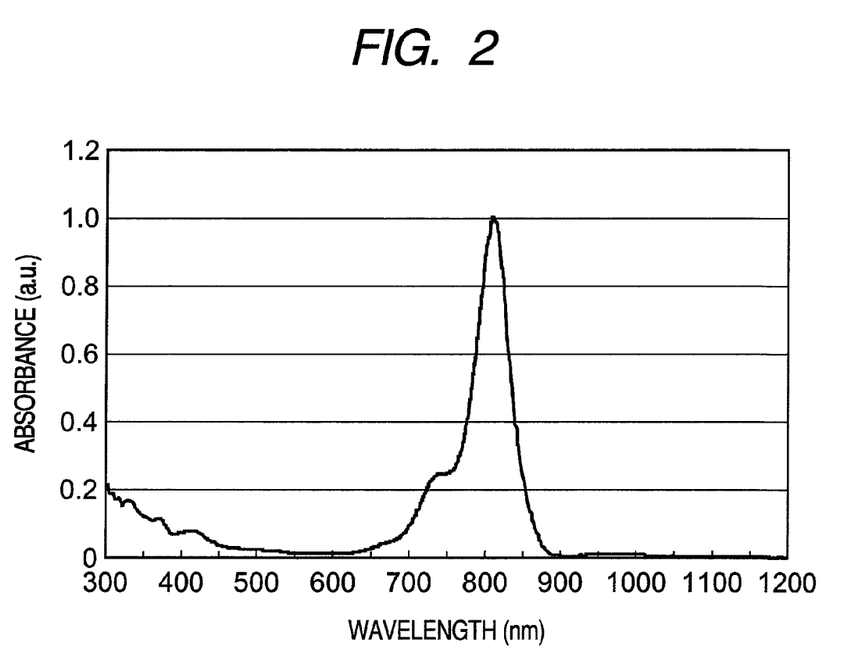
FIG. 2 is a graph showing a visible-near infrared absorption spectrum of the perimidine-substituted squarylium dye synthesized in Example 1.

The perimidine-substituted squarylium dye obtained is dissolved in tetrahydrofuran, and subjected to absorption spectrum measurements in the visible and near infrared regions. The result obtained is shown in FIG. 2. The absorption maximum wavelength $\lambda_{max}$ of the perimidine-substituted squarylium dye is found to be 811 nm (in the tetrahydrofuran solution).

(UV Irradiation Test)

Figure 3:
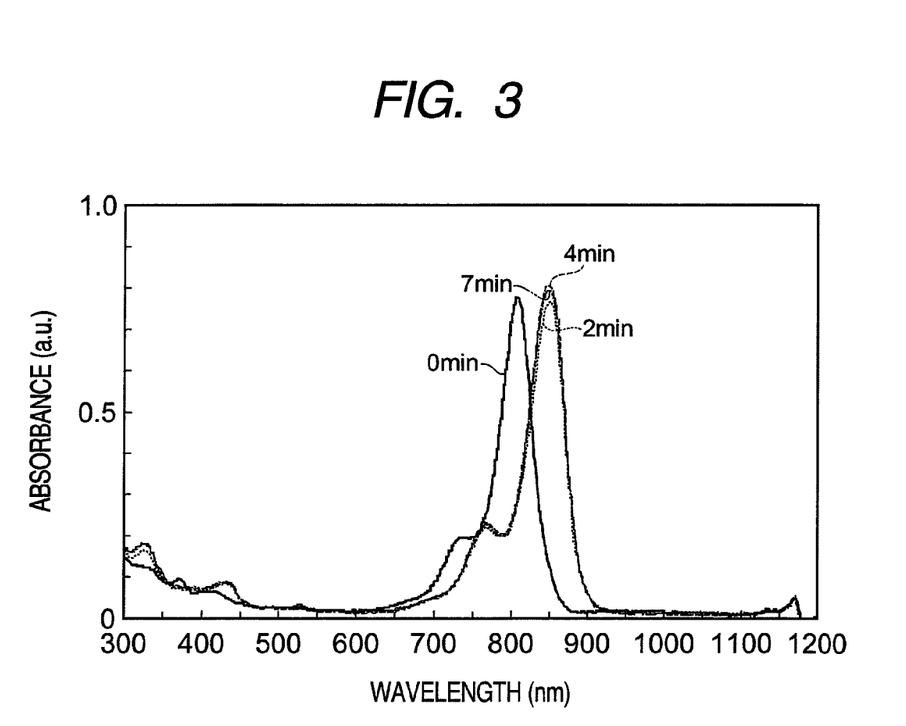
FIG. 3 is a graph showing changes which the perimidine-substituted squarylium dye synthesized in Example 1 produces in its infrared absorption spectrum under UV irradiation, wherein 1 denotes Dispersion medium, 2 denotes Holding member, and 10 denotes Detection medium.

A 0.001 mass % THF solution of the perimidine-substituted squarylium dye obtained in Example 1 is irradiated with UV light (Mineralight Lamp UVGL-25, trade name, a product of UVP Inc., wavelength: 365 nm, radiation illuminance: 2 mV/cm$^2$). Absorption spectra of the perimidine-substituted squarylium dye solution in the visible and near-infrared regions are measured before the UV irradiation, after 2-minute UV irradiation, after 4-minute UV irradiation and 7-minute UV irradiation, respectively. The results obtained are shown in FIG. 3. The absorption maximum wavelength $\lambda_{max}$ of the perimidine-substituted squarylium dye after 7-minute UV irradiation is found to be 850 nm (in the tetrahydrofuran solution).

Comparative Example 1

(Synthesis of Perimidine-Substituted Squarylium Dye)

A solution prepared by mixing 4.843 g (98%, 30.0 mmol) of 1,8-diaminonaphthalene, 3.886 g (98%, 30.2 mmol) of 3,5-dimethylcyclohexane and 10 mg (0.053 mmol) of p-toluenesulfonic acid monohydrate with 45 ml of toluene is heated up to 140° C. with stirring in an atmosphere of nitrogen gas, and refluxed at 140° C. for 5 hours. The water produced in the reaction is removed by component distillation. After the conclusion of the reaction, a dark brown solid obtained by distilling the toluene out of the reaction solution is dissolved in and extracted with acetone, purified by re-crystallization from an acetone-ethanol mixed solvent, and further dried at 110° C. Thus, 7.48 g of a brown solid as the intermediate is obtained (in 93.6% yield).

A solution prepared by mixing 4.69 g (17.6 mmol) of the intermediate obtained and 913 mg (8.0 mmol) of 3,4-dihydroxycyclobuta-3-ene-1,2-dione with 40 mL of n-butanol and 60 mL of toluene is heated up to 140° C. with stirring in an atmosphere of nitrogen gas, and refluxed at 140° C. for 3 hours, thereby running reaction. The water produced in the reaction is removed by component distillation. After the conclusion of the reaction, most of the solvents are distilled away in an atmosphere of nitrogen gas, and the reaction mixture obtained is added to 120 mL of hexane with stirring. The thus formed blackish brown precipitate is filtered off by suction, washed with hexane and dried, thereby yielding a blackish blue solid. This solid is washed with successive ethanol, acetone, a 60% aqueous solution of ethanol, ethanol and acetone. Thus, 4.30 g of perimidine-substituted squarylium dye represented by the following formula (II) is obtained in the form of a blackish blue solid (in 88% yield).

(II)

The perimidine-substituted squarylium dye obtained is dissolved in tetrahydrofuran, and subjected to absorption spectrum measurements in the visible and near infrared regions. The absorption maximum wavelength $\lambda_{max}$ of the perimidine-substituted squarylium dye is found to be 809 nm (in the tetrahydrofuran solution).

(UV Irradiation Test)

A 0.001 mass % THF solution of the perimidine-substituted squarylium dye obtained in Comparative Example 1 is irradiated with UV light (Mineralight Lamp UVGL-25, trade name, a product of UVP Inc., wavelength: 365 nm, radiation illuminance: 2 mV/cm$^2$). When visible and near-infrared absorption spectra of the perimidine-substituted squarylium dye solution after 7-minute UV irradiation is measured, it is found that the absorption maximum wavelength $\lambda_{max}$ of the spectra measured is 809 nm (in the tetrahydrofuran solution) and the spectra measured undergoes almost no change from the visible and near-infrared absorption spectra of the dye solution before UV irradiation.

Example 2

(Making of Fine Particles)

In a ball mill vessel, 50 mg of the perimidine-substituted squarylium dye synthesized in Example 1, 0.5 mL of a 0.1% aqueous solution of sodium dodecylbenzenesulfonate and 10 g of zirconia beads having a diameter of 1 mm are placed, and subjected to 1-hour milling treatment. Then, water is added to the ball mill vessel, and the perimidine-substituted squarylium dye thus levigated (hereinafter referred to as "fine Particles (A)) is collected by passage through a 50-nm filter. The median particle diameter d50 of the fine Particles (A) is found to be about 237 nm.

(Preparation of Slurry)

Slurry is prepared by subjecting 4.8 mg of fine Particles (A), together with 24 µL of a 12% aqueous solution of sodium dodecylbenzenesulfonate and 2.88 mL of distilled water, to ultrasonic dispersion treatment (ultrasonic power: 4-5 W, use of a ¼-inch horn, irradiation time: 60 minutes). The sample concentration in the slurry is found to be 0.165% by mass.

(Making of Slurry-Coated Paper and Evaluation of Color Performance)

A mixture of 37 µL of the slurry of fine Particles (A) (0.165 mass % in sample concentration), 15 µL of a 40 mass % latex (styrene-n-butyl acrylate copolymer) solution and 5 g of distilled water is subjected to dispersion treatment with an ULTRA-TURRAX, thereby preparing mixed slurry. To the mixed slurry thus obtained, a polyaluminum chloride flocculant is added to prepare a dispersion liquid of pseudo-toner. This pseudo-toner dispersion liquid is passed through a 0.22-µm filter, air-dried and further subjected to thermocompression bonding (120° C., mode 1), thereby preparing a latex patch (slurry-coated paper) for evaluation. Additionally, the latex patch for evaluation is a patch having resin film in which the total content of the color material and the styrene-acrylate resin latex (the mass of solids) is 4.5 g/m$^2$ as expressed in terms of gram number per square meter (TMA) and the content of the color material (PMA) is 0.045 g/m$^2$ (corresponding to 1.0 mass % as expressed in terms of content proportion of the color material to the resin).

This latex patch for evaluation is adopted as a sample and measured for a reflectance at 850 nm and L*, a* and b* values used in the L*a*b* color space by use of a spectrophotometer U-4100 (trade name, made by Hitachi Ltd.) and a calorimeter X-Rite 939 JP (trade name, made by X-Rite, Incorporated). By using the L*, a* and b* values, a color difference ΔE between the sample and C2 paper is determined, and invisibility of the sample can be quantified. The smaller reflectance value translates into the higher near-infrared absorptivity, and the smaller ΔE value translates into the higher invisibility. The results obtained are shown in Table 1.

Comparative Example 2

(Making of Fine Particles)

In a ball mill vessel, 50 mg of the perimidine-substituted squarylium dye synthesized in Comparative Example 1, 1 mL of hexane and 10 g of zirconia beads having a diameter of 1 mm are placed, and subjected to 1-hour milling treatment. Then, water is added to the ball mill vessel, and the perimidine-substituted squarylium dye thus levigated (hereinafter referred to as "fine Particles (B)) is collected by passage through a 50-nm filter. The median particle diameter d50 of the fine Particles (B) is found to be about 323 nm.

(Preparation of Slurry)

Slurry is prepared by subjecting 9.2 mg of fine Particles (B), together with 46 µL of a 12% aqueous solution of Triton X-100 and 5.52 mL of distilled water, to ultrasonic dispersion treatment (ultrasonic power: 4-5 W, use of a ¼-inch horn, irradiation time: 30 minutes). The sample concentration in the slurry is found to be 0.165% by mass.

(Making of Slurry-Coated Paper and Evaluation of Color Performance)

A mixture of 40.4 µL of the slurry of fine Particles (B) (0.165 mass % in sample concentration), 15 µL of a 40 mass % latex (styrene-n-butyl acrylate copolymer) solution and 5 g of distilled water is subjected to dispersion treatment with an ULTRA-TURRAX, thereby preparing mixed slurry. To the mixed slurry thus obtained, a polyaluminum chloride flocculant is added to prepare a dispersion liquid of pseudo-toner. This pseudo-toner dispersion liquid is passed through a 0.22-µm filter, air-dried and further subjected to thermocompression bonding (120° C., mode 1), thereby preparing a latex patch (slurry-coated paper) for evaluation. Additionally, the latex patch for evaluation is a patch having resin film in which the total content of the color material and the styrene-acrylic resin latex (the mass of solids) is 4.5 g/m$^2$ as expressed in terms of gram number per square meter (TMA) and the content of the color material (PMA) is 0.045 g/m$^2$ (corresponding to 1.0 mass % as expressed in terms of content proportion of the color material to the resin).

This latex patch for evaluation is adopted as a sample and, in accordance with the same method as in Example 2, reflectance of the sample at 850 nm and a color difference ΔE between the sample and C2 paper are determined. The results obtained are shown in Table 1.

Comparative Example 3

(Making of Fine Particles)

In a ball mill vessel, 50 mg of a vanadyl phthalocyanine dye (vanadyl phthalocyanine manufactured by YAMAMOTO CHEMICALS Inc.), 0.5 mL of a 0.1% aqueous solution of sodium dodecylbenzenesulfonate and 10 g of zirconia beads having a diameter of 1 mm are placed, and subjected to 1-hour milling treatment. Then, water is added to the ball mill vessel, and the vanadyl phthalocyanine dye thus levigated (hereinafter referred to as "fine Particles (C)) is collected by passage through a 50-nm filter. The median particle diameter d50 of the fine Particles (C) is found to be about 121 nm.

(Preparation of Slurry)

Slurry is prepared by subjecting 4.8 mg of fine Particles (C), together with 50 µL of a 12% aqueous solution of sodium dodecylbenzenesulfonate and 2.88 mL of distilled water, to ultrasonic dispersion treatment (ultrasonic power: 4-5 W, use of a ¼-inch horn, irradiation time: 60 minutes). The sample concentration in the slurry is found to be 0.165% by mass.

(Making of Slurry-Coated Paper and Evaluation of Color Performance)

A mixture of 37 µL of the slurry of fine Particles (C) (0.165 mass % in sample concentration), 15 µL of a 40 mass % latex (styrene-n-butyl acrylate copolymer) solution and 5 g of distilled water is subjected to dispersion treatment with an ULTRA-TURRAX, thereby preparing mixed slurry. To the mixed slurry thus obtained, a polyaluminum chloride flocculant is added to prepare a dispersion liquid of pseudo-toner. This pseudo-toner dispersion liquid is passed through a 0.22-µm filter, air-dried and further subjected to thermocompression bonding (120° C., mode 1), thereby preparing a latex patch (slurry-coated paper) for evaluation. Additionally, the latex patch for evaluation is a patch having resin film in which the total content of the color material and the styrene-acrylate resin latex (the mass of solids) is 4.5 g/m$^2$ as expressed in terms of gram number per square meter (TMA) and the content of the color material (PMA) is 0.045 g/m$^2$ (corresponding to 1.0 mass % as expressed in terms of content proportion of the color material to the resin).

This latex patch for evaluation is adopted as a sample and, in accordance with the same method as in Example 2, reflectance of the sample at 850 nm and a color difference ΔE between the sample and C2 paper are determined. The results obtained are shown in Table 1.

TABLE 1

| Sample | Initial Reflectance R [%] | ΔE |
|---|---|---|
| Example 2 | 38.47 | 12.4 |
| Comparative Example 2 | 42.3 | 6.7 |
| Comparative Example 3 | 45.5 | 32.4 |

What is claimed is:

1. A perimidine-substituted squarylium dye represented by the following formula (I):

(I)

2. A dispersion medium comprising:

the perimidine-substituted squarylium dye according to claim 1.

3. The dispersion medium according to claim 2, further comprising:

a polymer that the perimidine-substituted squarylium dye is dispersed in.

4. A detection medium comprising:

a holding member that is ultraviolet ray transmissive; and the dispersion medium according to claim 2 that is held to the holding member.

5. An image forming material, comprising:

the perimidine-substituted squarylium dye according to claim 1.

6. The image forming material according to claim 5, which is an electrophotographic toner; inkjet printer ink; or an ink for letterpress printing, offset printing, flexographic printing, gravure printing or silk-screen printing.

* * * * *